United States Patent [19]
Gold et al.

[11] Patent Number: 5,707,796
[45] Date of Patent: Jan. 13, 1998

[54] METHOD FOR SELECTING NUCLEIC ACIDS ON THE BASIS OF STRUCTURE

[75] Inventors: Larry Gold, Boulder, Colo.; Bruce Beutel, Suffern, N.Y.

[73] Assignee: NeXstar Pharmaceuticals, Inc., Boulder, Colo.

[21] Appl. No.: 198,670

[22] Filed: Feb. 22, 1994

Related U.S. Application Data

[63] Continuation of Ser. No. 960,093, Oct. 14, 1992, abandoned, which is a continuation-in-part of Ser. No. 536,428, Jun. 11, 1990, abandoned, and Ser. No. 714,131, Jun. 10, 1991, Pat. No. 5,475,096.

[51] Int. Cl.$^6$ .................... C07H 21/04; C07H 21/02; C12P 19/34; C12Q 1/68
[52] U.S. Cl. .................... 435/6; 435/91.2; 435/962; 435/973; 536/25.4; 935/77; 935/78
[58] Field of Search .................... 435/6, 91.2, 962, 435/973; 935/77, 78; 536/25.4

[56] References Cited

U.S. PATENT DOCUMENTS

| | | | |
|---|---|---|---|
| 4,833,092 | 5/1989 | Geysen | 435/6 |
| 5,133,866 | 7/1992 | Kauvar | 435/6 |
| 5,270,163 | 12/1993 | Gold et al. | 435/6 |

FOREIGN PATENT DOCUMENTS

| | | |
|---|---|---|
| 88307102 | 8/1988 | European Pat. Off. . |
| 2 183 661 | 6/1987 | United Kingdom . |
| WO 89/06694 | 7/1989 | WIPO . |
| PCT/US91/ 04078 | 6/1991 | WIPO . |
| PCT/US91/ 06793 | 9/1991 | WIPO . |
| WO 92/14843 | 9/1992 | WIPO . |

OTHER PUBLICATIONS

Bracco et al. (1989) The EMBO Journal 8:4289.
Gartenberg & Crothers (1991) J. Mol. Biol. 219:217.
Lilley (1991) Nature 354:359.
Tanaka et al. (1992) Mol. Gen. Genet. 226:367.
Goodman & Nash (1989) Nature 341:251.
Hagerman (1990) Ann. Rev. Biochem. 59:755.
Tuerk & Gold (1990) Science 249:505.
Marini et al. (1982) Proc. Natl. Acad. Sci. 79:7661.
Koo et al. (1986) Nature 320:501.
Diekmann (1987) in Nucleic Acids and Molecular Biology vol. 1:138.
Milton et al. (1990) Nucleic Acids Research 18:817.
Milton et al. (1990) J. Mol. Biol. 213:135.
Shatzky-Schwartz et al. (1992) Biochemistry 31:2339.
Kidson (1969) Biochemistry 8:4376.
Kuo, et al. (1986) J. Crhomatogr. Biomed. Applns. 378:361.
Linial, et al. (1988) Nucleic Acids Res., 16:6477.
Kidson, C., "Analysis of DNA Structures by Partition Chromatography", Biochemistry 8(11):4376–4382 (1969), (Abstr.).
Kuo, K.C. et al., "Quantitative Measurement of Messenger RNA CAP–0 and CAP–1 Structures by HPLC", J. Chromatogr. Biomed. Applns 378(2):361–374 (1986), (abstr).
Linial, M. et al., "Bent DNA Structures Associated With Several Origins of Replication are Recognized . . . ", Nuc Acids Res 16 (14A):6477–6492 (1988), (abstr.).
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Orita et al. PNAS, USA 86:2766–2770 (Apr. 1989).
Orita et al. Genomics 8:271–278 (1990).

Primary Examiner—Stephanie W. Zitomer
Attorney, Agent, or Firm—Swanson & Bratschun LLC

[57] ABSTRACT

A method of selecting nucleic acids on the basis of physical structure is disclosed. A modification of the Systematic Evolution of Ligands by Exponential enrichment (SELEX) is used in conjunction with methods for differentiating between nucleic acid molecules on the basis of physical structure, such as chromatography, gel electrophoresis, solubility, and solvent partitioning. The disclosed method may be used in selecting single stranded DNA or RNA, or double stranded DNA or RNA. An example of the method selected nucleic acids of bent DNA. This method represents a new and powerful approach to select nucleic acid molecules with the physical structure required for specific biological activity, for example, in the regulation of gene expression.

9 Claims, 7 Drawing Sheets

30N:   5'-CCCGTCGACAAAGCTGTTTAGCTAC[30N]CAGCATGCTCGACAGGCATCT-3'   SEQ ID NO:33

5' Primer: 5'-CCGAAGCTTAATACGACTCACTATAGGGAGATGCCTGTCGAGCATGCTG-3'   SEQ ID NO:34

3' Primer: 5'-CCCGTCGACAAAGCTGTTTAGCTAC-3'   SEQ ID NO:35

↓ PCR

30N DNA (104 Base pairs):

5'-CCGAAGCTTAATACGACTCACTATAGGGAGATGCCTGTCGAGCATGCTG[30N]GTAGCTAAACAGCTTTGTCGACGGG-3'  SEQ ID NO:36
3'-GGCTTCGAATTATGCTGAGTGATATCCCTCTACGGACAGCTCGTACGAC[30N]CATCGATTTGTCGAAACAGCTGCCC-5'  SEQ ID NO:37

FIG. 1

METHOD FOR SELECTING NUCLEIC ACIDS ON THE BASIS OF STRUCTURE

This is a continuation of application Ser. No. 07/960,093 filed on Oct. 14, 1992, now abandoned which is a Continuation-in-Part of U.S. patent application Ser. No. 07/536,428, filed Jun. 11, 1990, now abandoned, and 07/714,131, filed Jun. 10, 1991, now U.S. Pat. No. 5,475,096.

This work was supported by grants from the United States Government funded through the National Institutes of Health. The U.S. Government has certain rights in this invention.

FIELD OF THE INVENTION

This invention relates to the field of nucleic acids, specifically to a method of selecting nucleic acid molecules based on the physical structure of the molecule. The method disclosed herein is a modification of the SELEX technology, an acronym for Systematic Evolution of Ligands by Exponential enrichment. Specifically, SELEX is used in conjunction with gel electrophoresis to select nucleic acid molecules of bent DNA. The method disclosed presents a new and powerful approach to select nucleic acid molecules with the physical structure required for specific biological activity, for example, in the regulation of gene expression. The method described herein allows differentiation of nucleic acid molecules, including single and double stranded DNA and RNA, on the basis of physical characteristics, including, physical structure, solubility, or partitioning behavior.

BACKGROUND OF THE INVENTION

Bent DNA was first observed in the kinetoplast DNA circles of tropical parasites (Marini et al. (1982) Proc. Natl. Acad. Sci. USA 79:7661–7668, correction (1983) Proc. Natl. Acad. Sci. USA 80:7678; Wu and Crothers (1984) Nature 305:509–513). The observation that bent DNA exhibits anomalously low gel-electrophoretic mobility has led to in vitro experiments designed to address questions of sequence and structure (reviewed by Diekmann (1987) DNA curvature, in Nucleic Acids and Molecular Biology (F. Eckstein and D. M. J. Lilley, eds.), Springer-Verlag (New York), 1:138–156; Crothers et al. (1990) J. Biol. Chem. 265:7093–7096; Hagerman (1990) Ann. Rev. Biochem. 59:755–781).

The primary sequence characteristic which has been shown to give a large angle of stable curvature in DNA consists of runs of homopolymeric dA.dT base pairs, commonly referred to as "A-tracts" in phase with the helical repeat of DNA or approximately one A-tract every 10.5 base pairs. This periodic occurrence of A-tracts allows the angle of deflection from the helical axis resulting from each A-tract to be additive, thus giving rise to a large overall bend in the DNA (Hagerman (1985) Biochemistry 24:7034–7037; Diekmann (1986) FEBS Lett. 195:53–56; Koo et al. (1986) Nature 320:501–506). The molecular explanation for the bend in each A-tract has been an issue of some dispute, with some groups arguing that the origin of the bend is in the inclination of each dinucleotide base step and others arguing that the A-tract cooperatively adopts a non B-form helix giving rise to an angle of deflection at the junctions with the B-form intervening sequences. These two models are generally referred to as the wedge model (Trifonov and Sussman (1980) Proc. Natl. Acad. Sci. USA 77:3816–3820; Ulanovsky and Trifonov (1987) Nature 308:509–513; Bolshoy et al. (1991) Proc. Natl. Acad. Sci. USA 88:2312–2316) and junction model (Selsin et al. (1979) J. Biol. Chem. 254:5417–5422; Diekmann (1986) FEBS Lett. 195:53–56; Koo et al. (1986) Nature 320:501–506), respectively.

Other sequences have also been observed to cause bending in DNA. The sequence most similar to the A-tract motif is AAATTT ($A_3T_3$) (Hagerman (1985) Biochemistry 24:7034–7037). DNA lacking A-tracts and $A_3T_3$ (non-tract DNA) has been shown to bend when the sequence contains particular periodic dinucleotides. These are presumably due to the kind of bending described by the wedge model, but the magnitudes of bending associated with this kind of "non-tract" bending is much smaller than that observed for A-tracts or $A_3T_3$ (Fujimura (1988) Nucleic Acids Res. 16:1987–1997; Milton et al. (1990) J. Mol. Biol. 213:135–140; Bolshoy et al. (1991) supra; Brukner et al. (1991) Nucleic Acids Res. 19:3549–3551).

Smaller modulations of the magnitude of bending have been correlated to the presence or absence of more subtle sequence characteristics. In A-tract bending, it has been widely believed that the sequence 5'-CAAAAT-3', in which the bases just 5' and 3' to the A-tract are C and T, respectively, enhance the bend slightly (junction bases). Not only is this sequence conserved in *L. tarentolae* bent DNA, but earlier experiments showed that simultaneously changing the junction bases to C (making 5'-CAAAAC-3') or G (making 5'-GAAAAG-3') decreased the bend (Koo et al. (1986) supra). In the intervening regions between the A-tracts or $A_3T_3$ tracts, Milton et al. (1990) Nucleic Acids Res. 18:817–820, showed that having G-tracts, such as in the sequence 5'AAAAAGGGGGAAAAA-3' (SEQ ID NO:1), also increases the overall bend in the DNA. The results were more clear, however, for the $A_3T_3$ sequences than for A-tracts, which made it appear that there were still some unknown sequence effects which were not taken into account.

While much of the work on bent DNA has been exclusively in vitro, primarily using differences in gel electrophoretic mobility which correlate to the degree of bending, there is evidence that bent DNA may play an important role in various in vivo processes such regulation of gene expression. Bent DNA has been shown to directly activate transcription in *E. coli* and at least partially accounts for the effect of the catabolite activator protein (CAP) on transcription (Bracco et al. (1989) Embo. J 8.4289; Gartenberg and Crothers (1991) J. Mol. Biol. 219:217–230; review by Lilley (1991) Nature 354:359–360). Mapping of bent DNA sequences to the *E. coli* genome has shown that most bent sequences are located very close to transcriptional start-sites (Tanaka et al. (1992) Mol. Gen. Genet. 226:367–376), similar in position to the location of the CAP binding site shown to activate transcription if replaced by a bent sequence. Other work has led to the conclusion that bent DNA is involved in mechanisms of DNA recombination (Goodman and Nash (1989) Nature 341:251–254) and has been implicated in a number of other in vivo processes in prokaryotes and eukaryotes (reviewed by Hagerman (1990) supra).

SELEX (Systematic Evolution of Ligands for Exponential Enrichment) is a method for identifying and producing nucleic acid ligands (Tuerk and Gold (1990) Science 249:505–510). The method involves selection from a mixture of candidates and step-wise iterations of structural improvement, using the same general selection theme, to achieve virtually any desired criterion of binding affinity and selectivity. Starting from a mixture of nucleic acids, the method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

BRIEF SUMMARY OF THE INVENTION

Hereby disclosed is a method for selecting nucleic acid molecules on the basis of physical characteristics, including physical structure, electrophoretic mobility, solubility, and partitioning behavior. The method of the present invention is distinguished from all previous methods in that it does not select for molecules based on their binding affinities, but rather selects molecules based on specific structural criteria. The SELEX technology can be modified to be used in conjunction with a number of methods which differentiate molecules on the basis of their physical structure to select for molecules with specific structural features. The examples herein disclosed represent a modification of SELEX technology such that the selection step is based on standard electrophoretic methods to select molecules possessing a specific electrophoretic characteristic, in this case with the unique electrophoretic behavior of bent DNA. However, the present invention is not limited to the use of SELEX technology with electrophoresis; rather, SELEX-like techniques may be used with any method that differentiates molecules on the basis of structural characteristics, for example, HPLC, column chromatography, and chromatographic methods in general, solubility in a particular solvent, or partitioning between two phases such as $H_2O/CHCl_3$ or dextran/PEG. Further, the present invention can be applied to nucleic acids in general, including single stranded DNA (ssDNA), single stranded RNA (ssRNA), double stranded DNA (dsDNA), and double stranded RNA (dsRNA).

This invention includes a method for identifying nucleic acid molecules from a candidate mixture of nucleic acids on the basis of a given structural characteristic comprising preparing a candidate mixture of nucleic acids, partitioning between members of the candidate mixture on the basis of a given structural behavior, and amplifying the selected molecules to yield a mixture of nucleic acids enriched for molecules with such specific physical structure.

In one embodiment of the present invention, nucleic acid molecules are partitioned on the basis of specific electrophoretic behavior so that the resulting mixture of nucleic acids is enriched for molecules of bent DNA.

BRIEF DESCRIPTION OF THE FIGURES

FIG. 1 shows DNA oligonucleotides and the PCR product. Sequences are shown for 76 nucleotide 30N template, 49 nucleotide 5' PCR primer which anneals to 30 N template, and 25 nucleotide 3' PCR primer which anneals to complement of the template. The 104 base pair double-stranded DNA product of the PCR reaction is shown for designation of "top" and "bottom" strands. The 5' PCR primer contains a T7 promoter sequence.

DETAILED DESCRIPTION OF THE INVENTION

Figure 2:
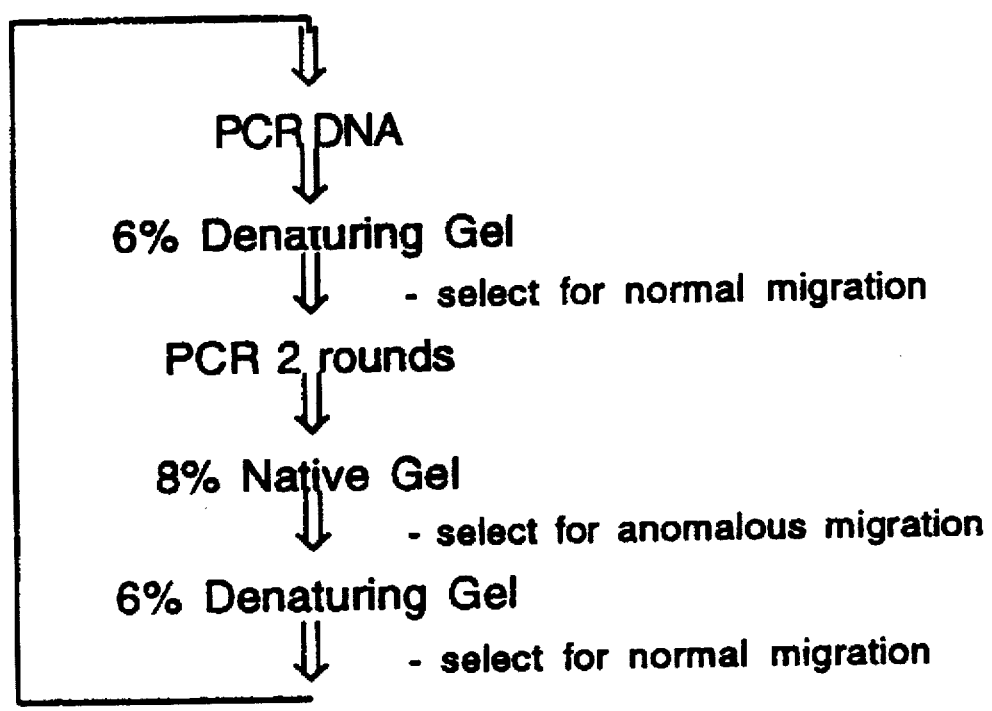
FIG. 2 is an outline of the SELEX-like procedure used to select nucleic acids on the basis of physical structure.

The present invention presents a method for selecting nucleic acid molecules on the basis of one or more specific physical characteristics. Prior methods have selected molecules on the basis of binding affinity. The method presented herein selects nucleic acid molecules solely on the basis of physical characteristics such as electrophoretic or chromatographic mobilities, solvent solubility, or partitioning behavior. The method of the present invention represents a modification of the SELEX technology (Tuerk and Gold (1990) Science 249:505-510). SELEX can be used in conjunction with any method which differentiates molecules on the basis of a structural property, such as electrophoretic mobility, chromatographic mobility, solubility, structure, or partitioning behavior.

This application is an extension of the method for identifying nucleic acid ligands referred to as SELEX. The SELEX method is described in detail in U.S. patent application Ser. No. 07/714,131 filed Jun. 10, 1991, entitled Nucleic Acid Ligands, now issued as U.S. Pat. No. 5,475, 096 and U.S. patent application Ser. No. 07/536,428 filed Jun. 11, 1990 entitled Systematic Evolution of Ligands by Exponential Enrichment now abandoned. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (i.e., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

The present invention represents a modification of the basic SELEX process described above wherein the partitioning step is comprised of any method which differentiates between molecules on the basis of a specific structural characteristic. The partitioning step may be based solely on differentiation on the basis of structural characteristics, or may be used in conjunction with the basic SELEX affinity selection.

In a nonlimiting example described herein, the anomalous migration of bent double stranded DNA on non-denaturing gels upon electrophoresis was used as a means of selecting DNA molecules of bent DNA. However, the disclosed invention is not limited to either differentiation on the basis of electrophoretic mobility or selection of bent DNA. The selection of nucleic acid molecules on the basis of specific structural characteristics can be accomplished with the use of the SELEX technology in conjunction with any methodology that differentiates molecules on the basis of some aspect of physical structure, including but not limited to chromatographic behavior, solubility in specific solvents, or partitioning behavior between two phases. The disclosed invention can be applied to any nucleic acid molecule, including ssDNA, ssRNA, dsDNA, or dsRNA.

In one embodiment of the invention, the partitioning of nucleic acids into a nonpolar solvent, such as $CHCl_3$, selects for a nucleic acid capable of entering nonpolar cellular structures, such as cell or nuclear membranes. A nucleic acid selected on such a basis is useful in delivery of nucleic acid (or other) drugs to a particular cellular location. In combination with the general SELEX procedure, one may select for a nucleic acid containing a "molecular switch", e.g., having one conformation in one environment and another in a different environment. For example, one may select for a nucleic acid which is compact while passing through a nonpolar cell membrane, which then unfolds to a less compact conformation inside the cell via a binding domain which is exposed upon entry into the polar cytoplasm, nucleus, or other cell compartment.

In the embodiment of the invention described in the Examples hereto, a region of 30 base pairs (bp) was completely randomized. The synthesis of oligonucleotides forming the initial populations of nucleic acids is described in Example 1. Example 2 describes the polymerase chain reaction methodology used to amplify the synthesized oligonucleotides. Example 3 describes electrophoretic procedures used in the partitioning process. An initial population of approximately $10^{12}$ different sequences was enriched by application of the modified SELEX method of the present invention for those DNA sequences which exhibited the kind of anomalous electrophoretic mobility associated with bent DNA. A population of 104 nucleotide length sequences were electrophoresed in a non-denaturing polyacrylamide gel. Those DNA sequences migrating with an apparent mobility of 114 bp were purified and electrophoresed on a denaturing polyacrylamide gel. Those migrating as 104 bp sequences in the denaturing gel were selected and used as templates in a PCR reaction, and the entire procedure was repeated seven times. Several new sequences were observed with characteristics which appear to be important to bending. The results significantly alter previously held beliefs about the effect of the junction and intervening sequences between A-tracts.

The term "A-tract" is used to mean either A-tracts or $A_3T_3$-like tracts unless otherwise noted. "A-tracts" refer to runs of 3–7 homopolymeric dA-dT base pairs, a primary sequence shown to give a large angle of stable curvature in DNA.

EXAMPLE 1

Synthesis of Oligonucleotides

Oligonucleotides were made on an Applied Biosystems 334 DNA synthesizer. The template strand for the duplex DNA contained 30 bases of mixed synthesis between two fixed regions. Template DNA (10 pmol) was amplified by PCR reaction with the corresponding primers (FIG. 1) to synthesize an initial pool of approximately 100 pmoles of double-stranded DNA fragments containing 30 bp of random or variable sequence. The populations contained approximately $10^{12}$ distinct sequences in the variable regions, flanked by 49 and 25 bp of fixed sequences.

EXAMPLE 2

PCR

PCR reactions were done in a Perkin-Elmer Thermal Cycler with incubations at 93° C. for 30 sec, 53° C. for 10 sec, and 72° C. for 4 min. Each reaction contained 500 pmoles of each primer, 2.5 mM $MgCl_2$, 10 mM Tris-Cl pH 8.4, 50 mM KCl, 170 µg/ml BSA, and 5 units Taq DNA polymerase (Promega) in a total volume of 100 µl. DNA from PCR reactions was phenol/chloroform extracted, ethanol precipitated, ethanol washed, and resuspended in TE (1 mM EDTA, 10 mM Tris-Cl pH 8.0) before loading on native polyacrylamide gels.

EXAMPLE 3

Electrophoresis and DNA Purification

All polyacrylamide gels contained 20:1 mono:bis with TBE (90 mM Tris-Borate, 2 mM EDTA, pH 8.0) used as the running buffer. Native gels were run 8–10 hours at 7 V/cm (except for the gel shown FIG. 7 which was run at 36 hours at 4 V/cm) and denaturing gels, which were 8 M urea, were run 2 hours at 25 V/cm. Standard loading dyes were used for native gels (5% glycerol, 0.1% bromophenol blue, and 0.1% xylene cyanol FF) and denaturing gels (80% formamide, 10 mM EDTA, 0.1% BB and 0.1% XC).

DNA was purified from polyacrylamide gels by freezing the gel slice containing the DNA of interest in an eppendorf tube in a dry ice/ethanol bath for 5 min., followed by the addition of 250 µl of 2 mM EDTA and 50 µl of 3M NaOAc and crushing with a plunger from a 1 ml syringe. The resulting slurry was forced through a 0.2 µm sterile cellulose acetate disk filter (Micro Filtration Systems) to remove all gel particles. After adding 2.5 volumes of ethanol and freezing at −70° C. for 5 min., the DNA was recovered by centrifugation for 15 min., followed by 70% ethanol wash and desiccation.

EXAMPLE 4

Selection of Bent DNA From a Random Population

A population of DNA fragments was purified away from PCR products of the wrong size (those other than 104 bp) by gel electrophoresis in a 6% denaturing polyacrylamide gel. The purified 104 nucleotide denatured DNA was made double-stranded and amplified slightly in a PCR reaction. Double-stranded DNA was then electrophoresed in a 8% native polyacrylamide gel, and DNA in the region of the gel which corresponded to the migration of a 114 bp marker was purified away from the vast majority of DNA which migrated to the expected position corresponding to 104 bp. The purified DNA was then repurified by electrophoresis in a 6% denaturing polyacrylamide gel at its proper migration corresponding to 104 nucleotides (rather than its apparent mobility of 114 bp on the native gel). This three gel selection procedure is summarized in FIG. 2. After the third gel purification, the DNA was again used as a template in a PCR reaction, and the entire procedure was repeated for seven rounds.

Figure 3:
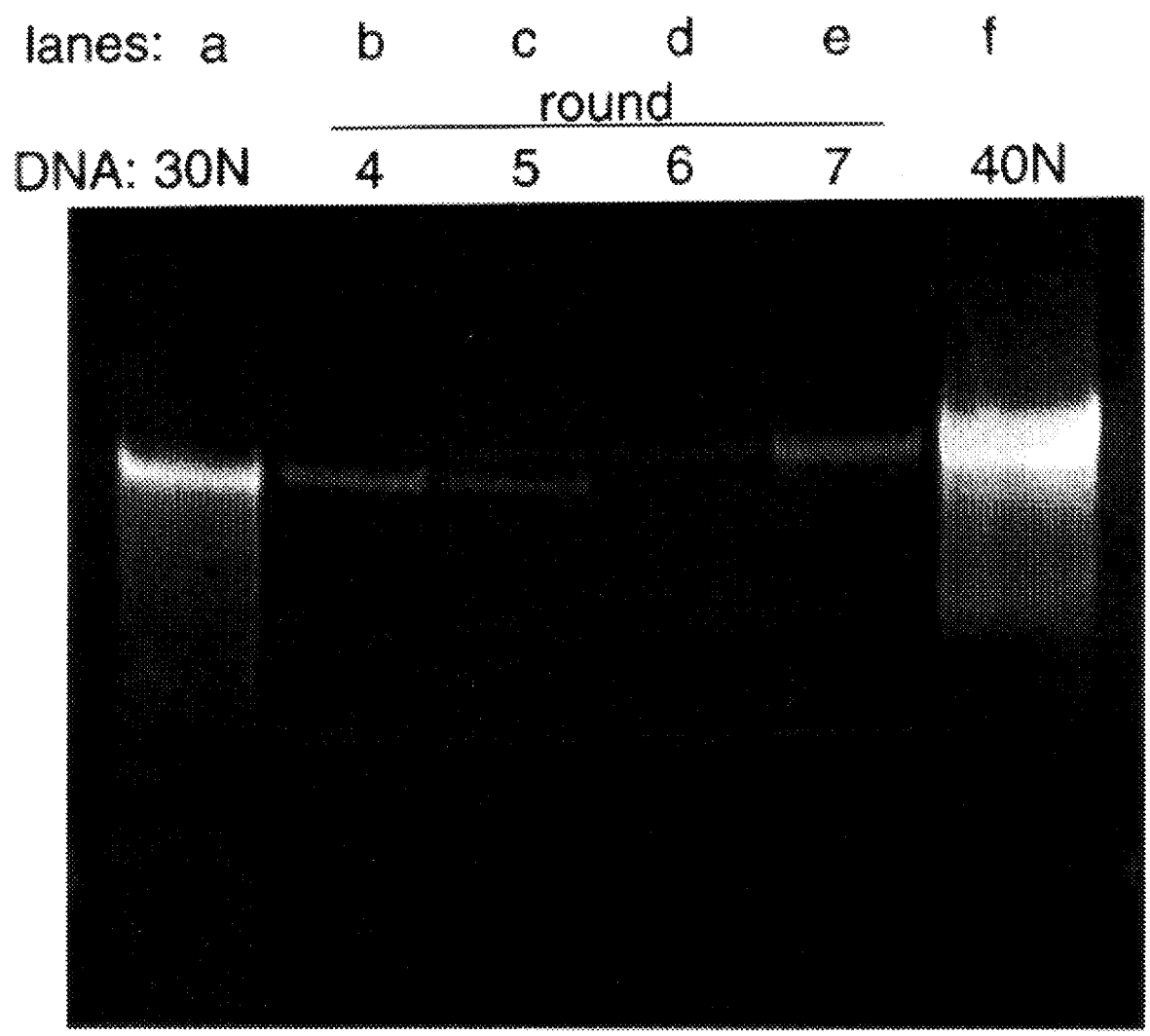
FIG. 3 shows the results of a SELEX-like selection. DNA migration in an 8% native gel is shown for initial 104 base pair 30N DNA used in round 1 (lane a), DNA which had been through 4-7 rounds of selection (lanes b-e), and 114 base pair DNA used as a marker for selection (lane f). The 114 base pair DNA is 40N DNA, which is identical to the initial 30N DNA except for the addition of 10 random base pairs to the random region. After each round of selection, 25% of the purified DNA was saved and amplified in PCR reactions to generate DNA. DNA was run and ethidium bromide stained on this gel. Note that after 5 rounds of selection (lane c) a significant portion of the DNA was migrating anomalously at 114 base pairs. Variation in intensity from lane to lane is due to variations in the amount of DNA loaded.
Figure 4:
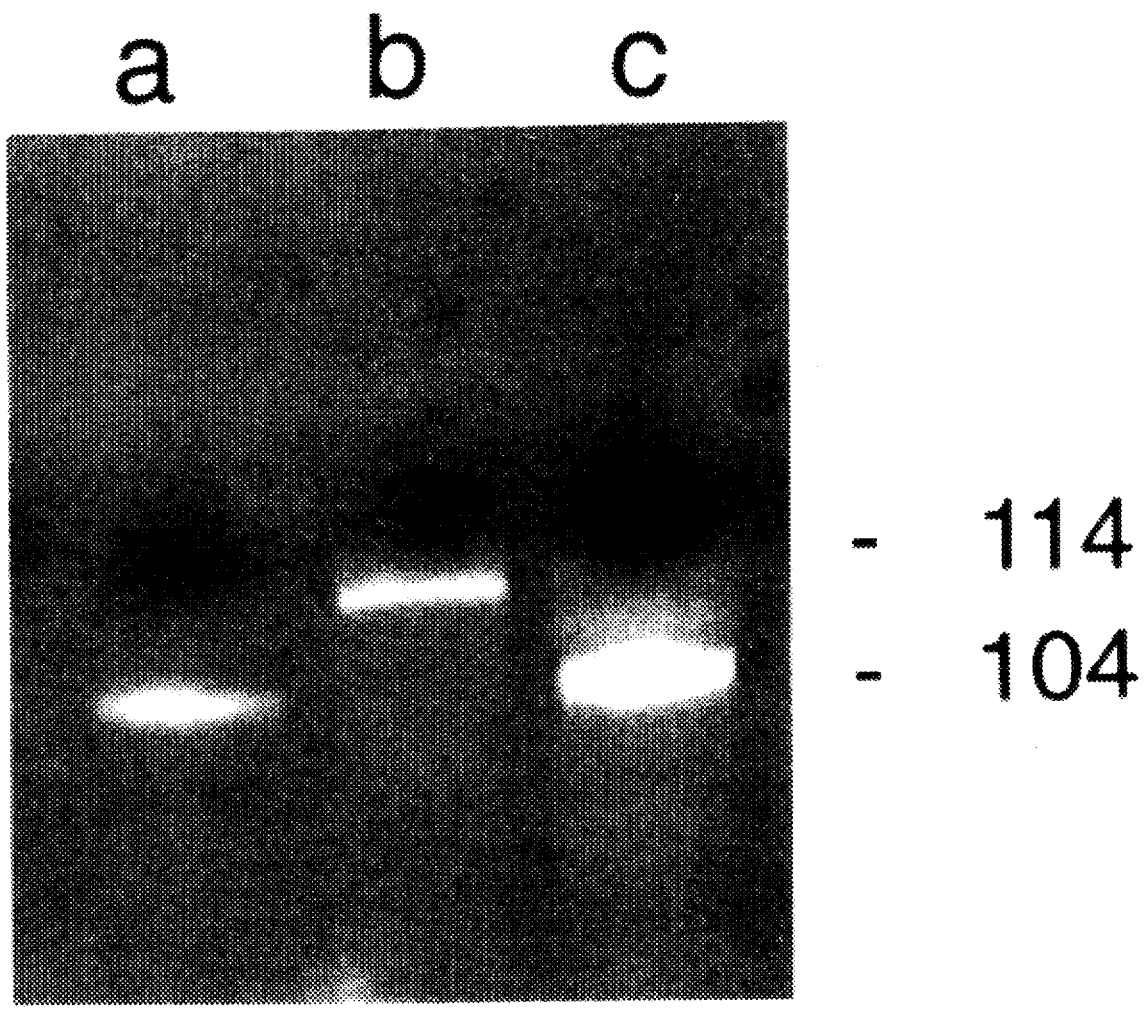
FIG. 4 shows the size of selected DNA on the denaturing gel. The migration in a 6% denaturing gel is shown for the selected bent DNA from round 7 (lane a), the 114 nucleotide marker (lane b), and initial 30N DNA (lane c). The gel was stained with ethidium bromide. The denatured selected DNA (lane a) migrates normally for its size of 104 nucleotides.

Double-stranded DNA from the initial population was compared to DNA from rounds 4–7 (FIG. 3). No visible amount of DNA migrated away from the initial migration of 104 bp until round 5. By round 7, all of the DNA which was visible by ethidium bromide migrated with an apparent size of 114 bp on the 8% native gel, while the same DNA when denatured migrated at is actual size of 104 nucleotides on a 6% denaturing gel (FIG. 4). DNA fragments from individual clones from the population of selected bent DNA were amplified by PCR and shown to migrate with the expected anomalous mobility (at 114 bp) that was exhibited by the round 7 population as a whole. There was a small amount of variation in the mobility of the individual selected sequences, but the variation was not large enough to correlate conclusively to sequence characteristics. The individual sequences, therefore, represent a narrow range of anomalous mobilities.

Of the 30 sequences obtained, 28 contain three A-tracts (or $A_3T_3$-like tracts) separated by approximately 10 bp (Table 1):

TABLE 1

Sequences of 30 Selected Bent DNA Fragments.
5'-CCGAAGCTTAATACGACTCACTATAGGGAGATGCCTGTCGAGCTG-30N-GTAGCTAAACAGCTTTGTCGACGGG-3' (SEQ ID NO: 2)

| Number | | Sequence in 30N region | | | | | | length |
|---|---|---|---|---|---|---|---|---|
| 1 | | TTTTT | ATCATA | TTTT | GACGAC | TTT | GGTGGG | 30 (SEQ ID NO: 3) |
| 2 | | TAATGTACCG | | TTTTT | AACG | TTTTTT | GGCGG | 30 (SEQ ID NO: 4) |
| 3 | | AAAAA | TGATGA | TTTT | CTTGGG | TTTT | AGCGG | 30 (SEQ ID NO: 5) |
| 4 | | TTTT | ATTGCCC | TTTTT | CCGTG | TTTTT | GACA | 30 (SEQ ID NO: 6) |
| 5 | | TTT | GCACCGA | TTTT | CGCGG | AAAA | CAGGGCAT | 31 (SEQ ID NO: 7) |
| 6 | | TTTTT | CATTG | AAA | TACGGC | TTTTTT | CATTG | 30 (SEQ ID NO: 8) |
| 7 | | TTTTT | GGCG | TTTTTT | GTCTG | TTTTT | GGAA | 29 (SEQ ID NO: 9) |
| 8 | | TTT | CTACCTGA | TTTT | CCCCTG | TTTT | ACGAGG | 31 (SEQ ID NO: 10) |
| 9 | | AAAA | TAACTCC | TTTTT | CCCTG | AATTTT | AGGCG | 32 (SEQ ID NO: 11) |
| 10 | | TTTT | GCATTGA | TTTT | GTTG | TTTTTT | GCCCG | 30 (SEQ ID NO: 12) |
| 11 | | TTTTT | CCTTGA | TTTT | AGCATG | TTTT | CGATC | 30 (SEQ ID NO: 13) |
| 12 | | AAAAA | CGTG | AATTT | GTGGTAGA | | TTCTACCC | 30 (SEQ ID NO: 14) |
| 13 | | AAAAA | CCCCA | TTTT | AGTCGTG | TTTTT | AGGC | 30 (SEQ ID NO: 15) |
| 14 | | TTTT | GACCTCG | TTTTT | GCCCGG | TTTT | GCAC | 30 (SEQ ID NO: 16) |
| 15 | A | TTT | AAGGTCG | TTTTT | CGGA | TTTTTT | GCCT | 30 (SEQ ID NO: 17) |
| 16 | C | AATTT | CCCAGG | TTTT | ACCCG | TTTTT | AGTG | 30 (SEQ ID NO: 18) |
| 17 | | TTTT | ACCCT | AAAA | CGGTCACA | TTTTT | CACT | 30 (SEQ ID NO: 19) |

TABLE 1-continued

Sequences of 30 Selected Bent DNA Fragments.
5'-CCGAAGCTTAATACGACTCACTATAGGGAGATGCCTGTCGAGCTG-30N-
GTAGCTAAACAGCTTTGTCGACGGG-3' (SEQ ID NO: 2)

| Number | Sequence in 30N region | | | | | | length |
|---|---|---|---|---|---|---|---|
| 18 | | AAATT | GCGTC | TTTTT | GGCATC | TTTTT | CATG | 30 (SEQ ID NO: 20) |
| 19 | | TTTT | GCCATGG | TTTTT | GTTA | TTTTT | CCGGTG | 31 (SEQ ID NO: 21) |
| 20 | | AAAAA | TACTCT | AAAAA | TGGCG | TTTT | CCTTG | 30 (SEQ ID NO: 22) |
| 21 | | AAAA | CCGT | AAAA | TCGGGGCG | TTTTT | GGCGT | 30 (SEQ ID NO: 23) |
| 22 | | TTTTT | CATCCA | TTTT | ACAGCAG | TTTT | GACCACT | 33 (SEQ ID NO: 24) |
| 23 | | TTTT | CCCCC | AATTT | GGGGTGA | TTTTT | GGCT | 30 (SEQ ID NO: 25) |
| 24 | A | TTTT | CCCGCG | TTTTT | AGCTA | TTTTTT | GTT | 30 (SEQ ID NO: 26) |
| 25 | | AAA | CAGTG | TTTTT | ATGAG | TTT | CAGCTCGCGT | 31 (SEQ ID NO: 27) |
| 26 | | TTTT | CGCAGA | TTTTT | CGAGCG | AAA | CACGTG | 30 (SEQ ID NO: 28) |
| 27 | CG | AAATT | GGCG | TTTTTTT | GGTCA | TTTTT | AC | 30 (SEQ ID NO: 29) |
| 28 | TCCA | TTTTT | ATGCAT | AAAA | TCACG | TTTT | AGC | 31 (SEQ ID NO: 30) |
| 29 | | AAATTT | GTCCG | AAATT | ACTGA | TTTTT | CTGG | 30 (SEQ ID NO: 31) |
| 30 | | AAA | TGAGCTG | AAAA | GGGCTA | TTTTT | AGCAC | 30 (SEQ ID NO: 32) |

Figure 5A:
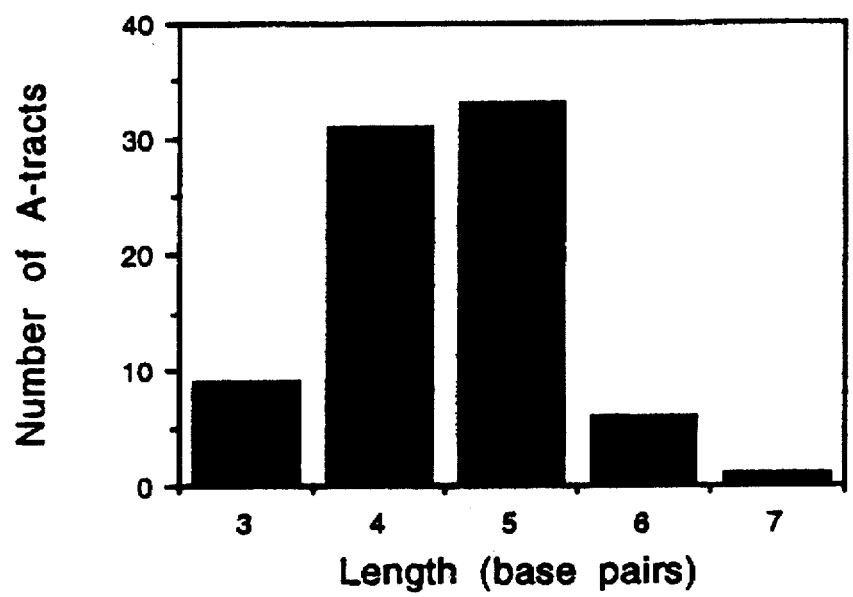
FIG. 5(a) shows the distribution of A-tract lengths. The lengths of A-tracts, excluding $A_3T_3$-like tracts, were scored for the 30 sequences of selected bent DNA shown in Table 1.
Figure 5B:
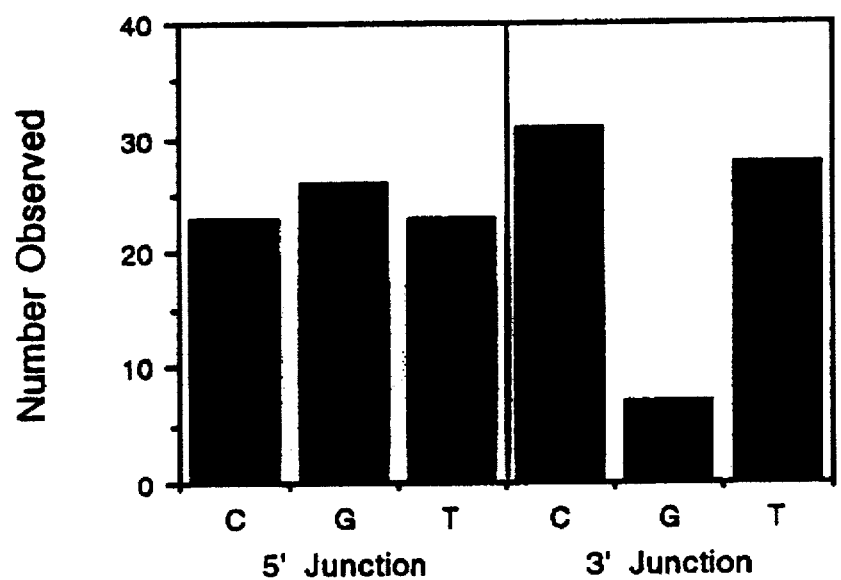
FIG. 5(b) shows the distribution of junction bases. The base sequences just 5' (left panel) and 3' (right panel) to A-tracts on the A-containing strand were scored for the 30 sequences. Only those sequences contained in the random region were scored. There are more 5' junctions than 3' junctions because of the high number of A-tracts which have a 3' end adjacent to the 49 base pair fixed sequence.

The other two sequences contain two A-tracts separated by approximately 10 bp. Therefore, non-tract bending motifs did not appear to be selected at a significant frequency. Approximately 9% of the tracts are of the $A_3T_3$ type, usually $A_3T_2$, and the other 91% are strictly A-tracts, varying in length from 3 to 7 bp each, as shown in FIG. 5a. There is a strong tendency for the A-tracts to be positioned with one A-tract as close as possible to the 59 bp fixed flanking region (the longer of the two flanking regions) with 80% of the sequences having an A-tract beginning with the first bp in the selected region. The periodicity of the middle of the A-tracts ($A_3T_3$-like tracts are not included in this calculation) is 10.3±1.0 bp. The frequencies of occurrence of bases 5' and 3' to each A-tract (not counting any $A_3T_3$-like tracts) are shown in FIG. 5b. The results clearly demonstrate that having a 3'-G lessens the bending, since G is the 3' junction base at only 10% of the junctions. At the other 3' junctions, C and T occur with equal frequencies. It has previously been observed that 3'-T increased the bend compared to 3'-C, which in turn was more bent than 3'-G.

Figure 6A:
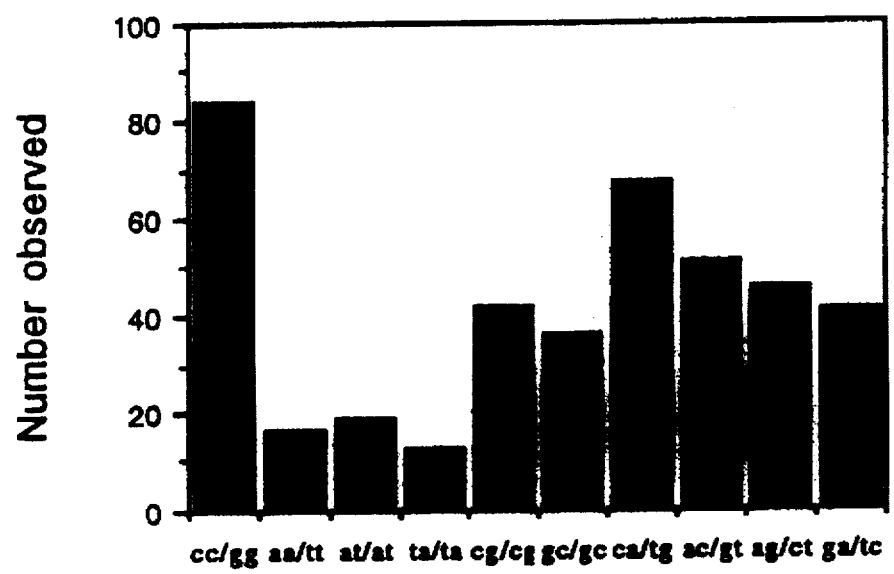
FIG. 6(a) shows the base step composition of intervening regions. The base steps in the intervening regions (non-tract sequences) were scored for the 30 sequences shown in Table 1.
Figure 6B:
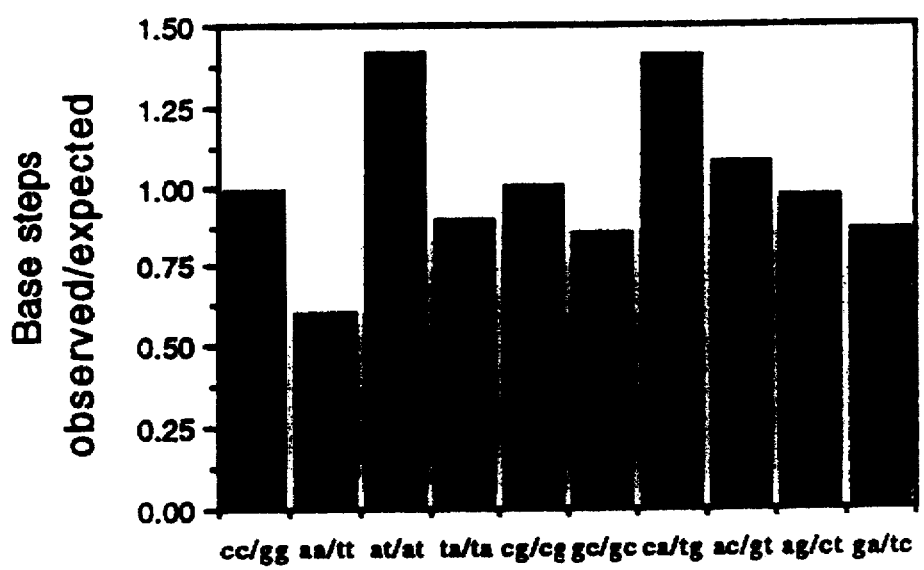
FIG. 6(b) shows the arrangement of base pairs into base steps. The base step composition shown in FIG. 6(a) is normalized to the number of base steps predicted based on the nucleotide frequencies observed in the intervening regions.

The regions between the A-tracts are 64% G+C rich, leading to the GG/CC base step being extremely overabundant. The frequencies of occurrence of each of the 10 base steps is shown in FIG. 6(a). The second most abundant base step is CA/TG. Both of these base steps are significantly over represented (over 95% confidence in a chi-squared analysis) in the set of 414 base steps that are located within the intervening regions. FIG. 6(b) shows the ratio of observed/expected frequency of the 10 base steps given the high G+C composition of the intervening regions. The highly abundant GG/CC base step only occurs as often as would be expected given the G+C richness of these regions. The CA/TG step, however, occurs far more frequently than expected, meaning that this particular arrangement or ordering of base pairs is predominant (more than, for example, the AC/GT base step which has the same composition). All base steps consisting of A/T only do not occur very often (FIG. 6a) because of the richness, but it is still interesting to note that the base step AA/TT occurs fewer times than expected, even given the G+C richness, while AT/AT occurs much more than expected (FIG. 6b). In other words, A/T sequences are not preferable in general, but there seems to be a preference for the particular arrangement of AT/AT over other arrangements of A/T base pairs. Because the absolute number of AT/AT base steps is so low, it does not occur at a frequency with statistical significance. However, upon closer examination it can be seen that 15 of the 19 occurrences of AT/AT are located in the sequences CAT/ATG. This is not many more than the 12 that would be expected given the overabundance of CA/TG. This indicates that the CA/TG base step appears to be the primary source of nonrandomness. The significantly low number of AA/TT base steps in the intervening regions are relatively easy to explain since by definition these are regions which first and foremost need to contain non A-tract sequences to provide the A-tract periodicity.

No sequences were observed occurring more than once in the sample of 30 sequences. Since the selection is noncompetitive (i.e., the entire DNA populations can migrate to the same position without competition), it should have selected all DNA fragments which were bent enough to migrate to the 114 base pair (or near 114) position on a native gel. This was apparently stringent enough to select against moderately bent sequences (such as non-tract sequences) and select for sequences which had the maximum number of A-tracts which could be fit into the 30 base pair random region, those which had the A-tracts positioned as close as possible to the center of the DNA fragment, and those which had important sequences located in other intervening regions. Even with this assortment of sequence characteristics, the collection of selected sequences migrates slightly faster than 114 base pairs, suggesting that the selection was very stringent. A rough calculation shows that an A-tract of average length 4.5 will occur twice (either polarity) in every $4^{4.5}$ sequences, or once in every 256. Three A-tracts will occur, therefore, approximately once in $256^3$ sequences, which is equal to once in $1.7 \times 10^7$ sequences. The nonrandom sequences in the intervening regions (G+C richness, CA/TG richness, junction preferences) are not as necessary as the A-tracts to the selection, but would still make the actual frequency of "winning" sequences a little lower. This is in good agreement with the estimation of a 20-fold enrichment per round of selection (estimated by the number of PCR cycles required to replenish the DNA to the original concentration), yielding a vast majority of bent DNA after 6 rounds (or a total enrichment of about $6 \times 10^7$). Starting with an initial population of about $10^{12}$ sequences, there should have been as many as $10^{12}/(1.7 \times 10^7) \approx 58,000$ unique sequences which would be enriched by the selection.

Sequences which barely met the selection criteria, by definition, would be more abundant in the original population than those which had more of the sequence characteristics being selected. However, those which met more criteria and were therefore more bent would be preferentially selected at the 114 base pair position. In other words, those at the 113 base pair position would be selected at a slightly lower enrichment per round than those at the 114 position, but there would be many more at the 113 position to be selected since fewer sequence requirements could cause that extent of bending. Because it would be prohibitive to sequence on the order of tens of thousands of clones in this experiment, 30 clones were sequenced, sufficient to show the statistical significance of the results.

A closer examination of the 30 sequences shows that there does appear to be the predicted trade-off between having all the sequence characteristics required for bending and being abundant in the initial population. There is a tendency for each sequence to have some, but not all, of the sequence characteristics associated with bending. For example, in 16 sequences with low (<3) numbers of CA/TG, the CC/GG base step occurs 57 times compared to only 27 times in the 14 sequences which have a high number (>2) of CA/TG. Another example is the 13 sequences which have the polarity of the A-tracts such that there are three tracts with T always on the top strand. These 13 sequences contain a total of 26 CA/TG base steps, which is only slightly more than the expected number. In the 15 sequences containing the three A-tracts of varying polarity, however, CA/TG occurs 38 times. In other words, given the variables of having A-tracts with a certain polarity, abundant CA/TG base steps, and abundant CC/GG base steps, individual sequences tend to have one or two of these variables but not all three. This is likely due to the explanation given above, namely, that sequences with proper polarity A-tracts separated by intervening regions which are highly G/C rich interrupted occasionally with CA/TG base steps would occur much more rarely in the initial population and would only have a slight advantage (if any) in the selection process. Therefore, the variables other than the requirement for periodic A-tracts are understood by the composition of the set of 30 sequences, rather than by an individual sequence in the population. The hypothesis which comes from this analysis is that A-tracts (including $A_3T_3$-like tracts) are necessary for a large part of this extent of bending, while the other variables each make minor contributions to the bend which when added together were necessary to meet the selection criteria.

EXAMPLE 5

Cloning and Sequencing of Bent DNA

DNA purified from the native gel in round 7 of Example 3 was cloned and sequenced. Purified DNA and puc118 plasmid DNA were digested with HindIII and BgIII restriction enzymes, followed by ligation and transformation into XL 1-Blue *E. coli* (Stratagene). Restriction digests, ligations, transformations, DNA minipreps, and dideoxy DNA sequencing were done by standard methods.

EXAMPLE 6

Role of CA/TG Base Steps in DNA Bending.

Synthetic DNA templates with sequences of #11, 11-M, and 30N were annealed with 5' primer and made double stranded in a Klenow reaction with labelled dCTP. After electrophoresis, an x-ray film was exposed to the gel for 4 hours to produce autoradiogram. The sequence of 11-M is identical to #11 except for the replacement of the 6 bases involved in CA and TG dinucleotides. In 11-M these 6 positions have random sequences. Note that the absence of these CA/TG base steps decreases the anomalous mobility of the DNA.

Figure 7:
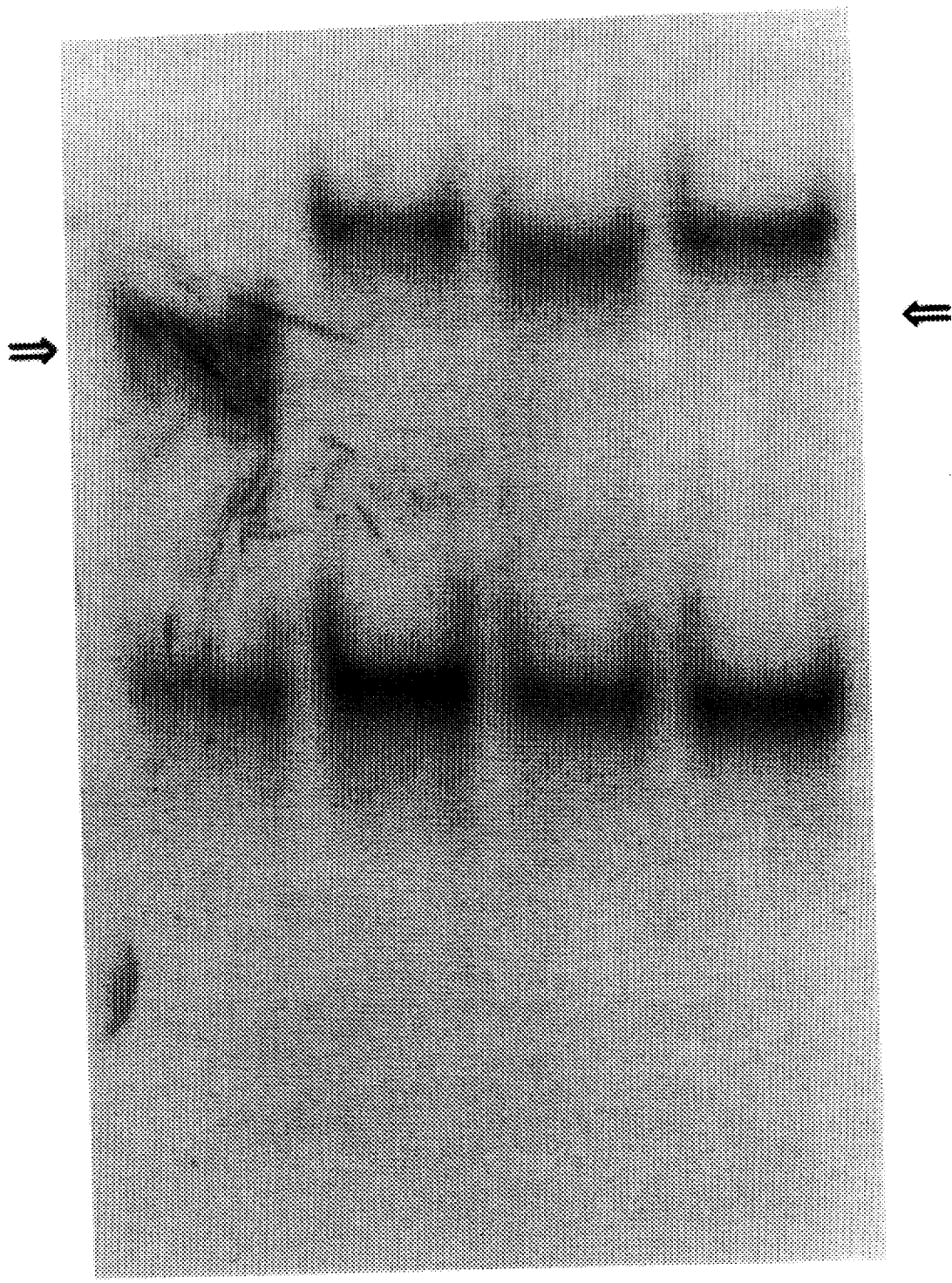
FIG. 7 shows the effect of CA/TG base step on DNA bending. The migration in an 8% native gel is shown (in the area pointed to by arrows) for 30N DNA (lane 1), #11 selected bent DNA (lanes 2, 4), and 11-M DNA (lane 3). The lower band in each lane is a spurious primer-primer annealing product which serves as an internal control for slight lane to lane variation in the gel.

The electrophoretic mobilities of two related synthetic DNA fragments were compared to directly test the conclusion that the unusually high frequency of CA/TG base steps in the selected DNA is a meaningful addition to the other known variables which have an effect on DNA bending. Two template strands were synthesized, one of which had the exact sequence of clone #11. The other, 11-M, had the same sequence except at the six nucleotide positions which are located in the 3 CA/TG base steps in clone #11. These six positions were randomized in the synthesis with the exclusion of nucleotides which would allow the reconstruction of CA or TG base steps in the template. Complementary strands were synthesized enzymatically, and the resulting DNA fragments were compared by electrophoresis (FIG. 7). The 11-M fragment, which is actually a small mixture of nearly identical fragments which differ from #11 only by the absence of the CA/TG base steps, clearly migrates slightly less anomalously than the #11 fragment. Approximately 10-15% of the anomalous mobility of #11 (compared to a normal 104 base pair fragment) is apparently due to some combination of the three CA/TG base steps in its A-tract intervening regions. The remainder of the anomalous mobility (and presumed bending) is due to the properly phased A-tracts themselves.

---

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AAAAAGGGGG AAAAA                                                                15

(2) INFORMATION FOR SEQ ID NO:2:

(i) SEQUENCE CHARACTERISTICS:
       (A) LENGTH: 100 base pairs
       (B) TYPE: nucleic acid
       (C) STRANDEDNESS: single
       (D) TOPOLOGY: linear (xi) SEQUENCE DESCRIPTION: SEQ ID NO:2:

CCGAAGCTTA ATACGACTCA CTATAGGGAG ATGCCTGTCG AGCTGNNNNN     50

NNNNNNNNNN NNNNNNNNNN NNNNNGTAGC TAAACAGCTT TGTCGACGGG    100

(2) INFORMATION FOR SEQ ID NO:3:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:3:

TTTTTATCAT ATTTTGACGA CTTTGGTGGG                            30

(2) INFORMATION FOR SEQ ID NO:4:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:4:

TAATGTACCG TTTTTAACGT TTTTTGGCGG                            30

(2) INFORMATION FOR SEQ ID NO:5:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:5:

AAAAATGATG ATTTTCTTGG GTTTTAGCGG                            30

(2) INFORMATION FOR SEQ ID NO:6:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:6:

TTTTATTGCC CTTTTTCCGT GTTTTTGACA                            30

(2) INFORMATION FOR SEQ ID NO:7:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:7:

TTTGCACCGA TTTTCGCGGA AAACAGGGCA T    31

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTTTTCATTG AAATACGGCT TTTTTCATTG    30

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTTTGGCGT TTTTTGTCTG TTTTTGGAA    29

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTTCTACCTG ATTTTCCCCT GTTTTACGAG G    31

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AAAATAACTC CTTTTTCCCT GAATTTTAGG CG    32

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTTTGCATTG ATTTGTTGT TTTTTGCCCG    30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TTTTTCCTTG ATTTTAGCAT GTTTCGATC    30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAAAACGTGA ATTTGTGGTA GATTCTACCC         30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

AAAAACCCCA TTTAGTCGT GTTTTAGGC         30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TTTTGACCTC GTTTTGCCC GGTTTTGCAC         30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

ATTTAAGGTC GTTTTCGGA TTTTTTGCCT         30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CAATTTCCCA GGTTTTACCC GTTTTTAGTG         30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TTTTACCCTA AAACGGTCAC ATTTTTCACT         30

( 2 ) INFORMATION FOR SEQ ID NO:20:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:20:

AAATTGCGTC TTTTTGGCAT CTTTTTCATG    30

( 2 ) INFORMATION FOR SEQ ID NO:21:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

TTTTGCCATG GTTTTTGTTA TTTTTCCGGT G    31

( 2 ) INFORMATION FOR SEQ ID NO:22:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

AAAAATACTC TAAAAATGGC GTTTTCCTTG    30

( 2 ) INFORMATION FOR SEQ ID NO:23:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

AAAACCGTAA AATCGGGGCG TTTTGGCGT    30

( 2 ) INFORMATION FOR SEQ ID NO:24:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

TTTTTCATCC ATTTTACAGC AGTTTTGACC ACT    33

( 2 ) INFORMATION FOR SEQ ID NO:25:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

TTTTCCCCCA ATTTGGGGTG ATTTTTGGCT    30

( 2 ) INFORMATION FOR SEQ ID NO:26:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:26:

ATTTTCCCGC GTTTTTAGCT ATTTTTTGTT                                30

(2) INFORMATION FOR SEQ ID NO:27:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:27:

AAACAGTGTT TTTATGAGTT TCAGCTCGCG T                              31

(2) INFORMATION FOR SEQ ID NO:28:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:28:

TTTTCGCAGA TTTTTCGAGC GAAACACGTG                                30

(2) INFORMATION FOR SEQ ID NO:29:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:29:

CGAAATTGGC GTTTTTTGG TCATTTTAC                                  30

(2) INFORMATION FOR SEQ ID NO:30:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:30:

TCCATTTTTA TGCATAAAAT CACGTTTTAG C                              31

(2) INFORMATION FOR SEQ ID NO:31:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:31:

AAATTTGTCC GAAATTACTG ATTTTCTGG                                 30

(2) INFORMATION FOR SEQ ID NO:32:

(i) SEQUENCE CHARACTERISTICS:
(A) LENGTH: 30 base pairs
(B) TYPE: nucleic acid (C) STRANDEDNESS: single
(D) TOPOLOGY: linear (xi) SEQUENCE DESCRIPTION: SEQ ID NO:32:

AAATGAGCTG AAAAGGGCTA TTTTTAGCAC                                    30

(2) INFORMATION FOR SEQ ID NO:33:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (xi) SEQUENCE DESCRIPTION: SEQ ID NO:33:

CCCGTCGACA AAGCTGTTTA GCTACNNNN NNNNNNNNNN NNNNNNNNN                 50

NNNNNCAGCA TGCTCGACAG GCATCT                                        76

(2) INFORMATION FOR SEQ ID NO:34:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (xi) SEQUENCE DESCRIPTION: SEQ ID NO:34:

CCGAAGCTTA ATACGACTCA CTATAGGGAG ATGCCTGTCG AGCATGCTG               49

(2) INFORMATION FOR SEQ ID NO:35:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:35:

CCCGTCGACA AAGCTGTTTA GCTAC                                         25

(2) INFORMATION FOR SEQ ID NO:36:

(i) SEQUENCE CHARACTERISTICS:
      (A) LENGTH: 104 base pairs
      (B) TYPE: nucleic acid
      (C) STRANDEDNESS: single
      (D) TOPOLOGY: linear (xi) SEQUENCE DESCRIPTION: SEQ ID NO:36:

CCGAAGCTTA ATACGACTCA CTATAGGGAG ATGCCTGTCG AGCATGCTGN               50

NNNNNNNNN NNNNNNNNNN NNNNNNNNG TAGCTAAACA GCTTTGTCGA                100

CGGG                                                                104

(2) INFORMATION FOR SEQ ID NO:37:

(i) SEQUENCE CHARACTERISTICS:
      (A) LENGTH: 104 base pairs
      (B) TYPE: nucleic acid
      (C) STRANDEDNESS: single
      (D) TOPOLOGY: linear (xi) SEQUENCE DESCRIPTION: SEQ ID NO:37:

| | | | | | |
|---|---|---|---|---|---|
| GGCTTCGAAT | TATGCTGAGT | GATATCCCTC | TACGGACAGC | TCGTACGACN | 50 |
| NNNNNNNNNN | NNNNNNNNNN | NNNNNNNNNC | ATCGATTTGT | CGAAACAGCT | 100 |
| GCCC | | | | | 104 |

We claim:

1. A method for identifying nucleic acid molecules from a candidate mixture of nucleic acids on the basis of a specific structural characteristic, comprising:
   a) subjecting said candidate mixture of nucleic acids to partitioning;
   b) selecting nucleic acids having said specific structural characteristic as determined by their partitioning behavior;
   c) amplifying the selected nucleic acids to yield an amplification mixture enriched for nucleic acids having the specific structural characteristic;
   d) repeating steps b) and c), whereby nucleic acid molecules having said specific structural characteristic may be identified.

2. The method of claim 1 wherein said partitioning is by gel electrophoresis.

3. The method of claim 2 wherein said structural characteristic is bent DNA.

4. The method of claim 1 wherein said structural characteristic is compact conformation.

5. The method of claim 1 wherein said partitioning is by exposure to a solvent.

6. The method of claim 1 wherein said partitioning is between two solvent phases.

7. The method of claim 1 wherein said nucleic acid is single or double stranded DNA.

8. The method of claim 1 wherein said nucleic acid is single or double stranded RNA.

9. The method of claim 1 wherein said partitioning is by chromatography.

* * * * *